United States Patent [19]

Mitra et al.

[11] Patent Number: 4,468,381

[45] Date of Patent: Aug. 28, 1984

[54] CONCENTRATED MAGNESIUM HYDROXIDE PREPARATIONS

[75] Inventors: Arun K. Mitra; Robert G. Flynn, both of St. Louis, Mo.

[73] Assignee: Norcliff Thayer, Inc., Tarrytown, N.Y.

[21] Appl. No.: 500,730

[22] Filed: Jun. 3, 1983

Related U.S. Application Data

[63] Continuation-in-part of Ser. No. 259,712, May 1, 1981, abandoned, which is a continuation-in-part of Ser. No. 872,995, Jan. 27, 1978, abandoned, which is a continuation-in-part of Ser. No. 724,454, Sep. 17, 1976, abandoned.

[51] Int. Cl.³ ............................................. A61K 33/08
[52] U.S. Cl. ................................................... 424/158
[58] Field of Search ................................ 424/156, 158

[56] References Cited

U.S. PATENT DOCUMENTS

| | | | |
|---|---|---|---|
| 2,087,089 | 7/1937 | Hall | 424/128 |
| 2,193,281 | 3/1940 | Hall | 424/128 |
| 3,062,714 | 11/1962 | Pitkin et al. | 424/157 |
| 3,245,876 | 4/1966 | Martin, Jr. | 424/157 |
| 3,579,634 | 5/1971 | Brown | 424/156 |
| 3,591,680 | 7/1971 | Greene et al. | 424/158 |
| 3,621,094 | 11/1971 | Mayron | 424/158 |
| 3,735,007 | 5/1973 | Lapidus et al. | 424/158 |

OTHER PUBLICATIONS

"Handbook of Non-Prescription Drugs", 1973 Edition, Pub. by The American Pharm. Assoc., Wash., D.C., pp. 65–69.

*Primary Examiner*—Frederick E. Waddell

[57] ABSTRACT

Stable aqueous thixotropic compositions containing from about 16 to 24% by wt./vol. of magnesium hydroxide are obtained by using an anionic polymer, a stabilizing or thixotropy producing agent and a thinning or fluidizing agent in a specific order of addition.

22 Claims, 12 Drawing Figures

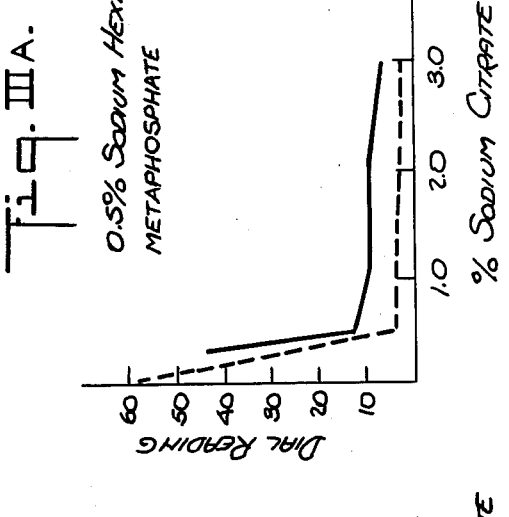
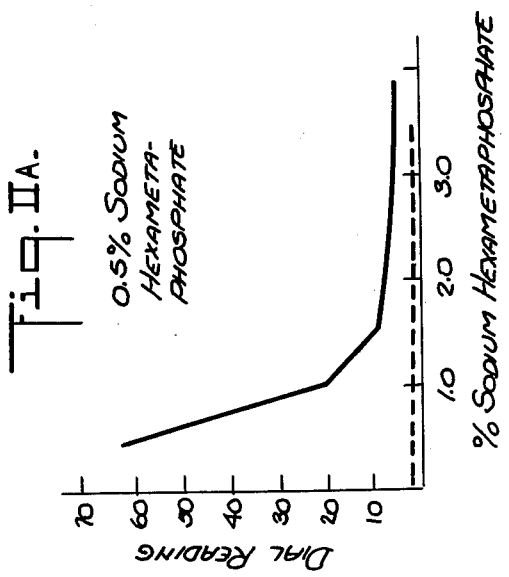
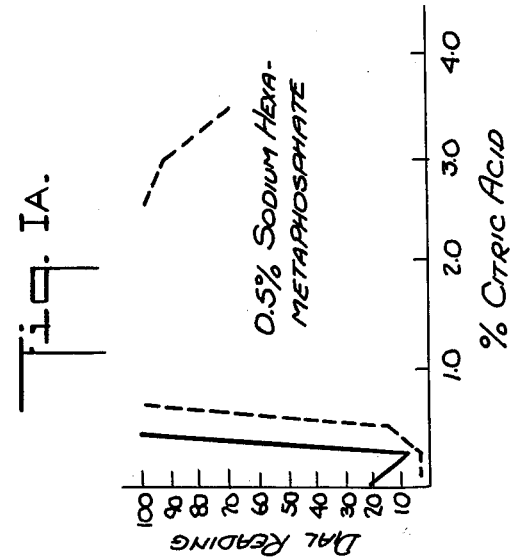
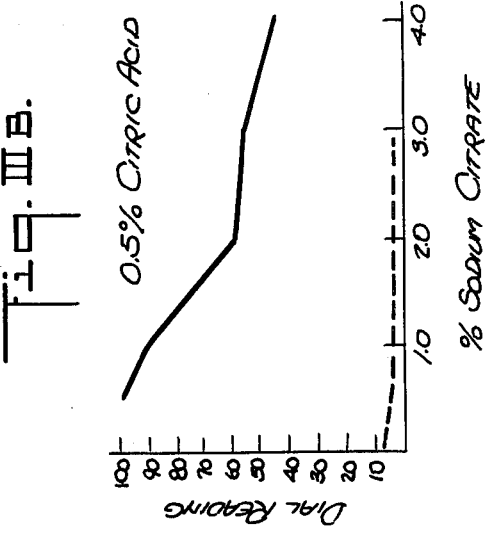
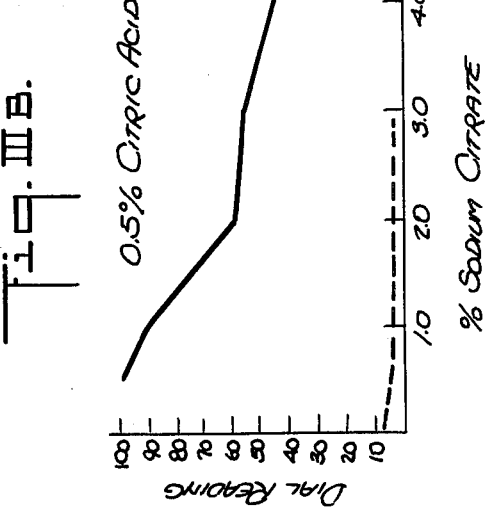
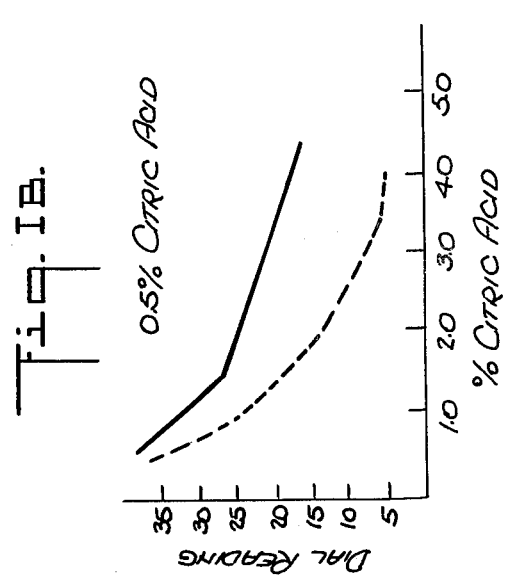

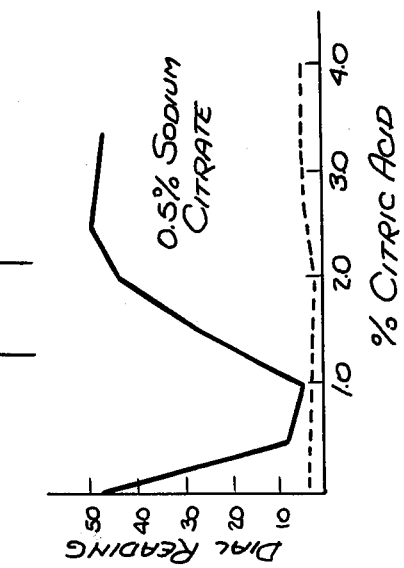
Fig. IC.
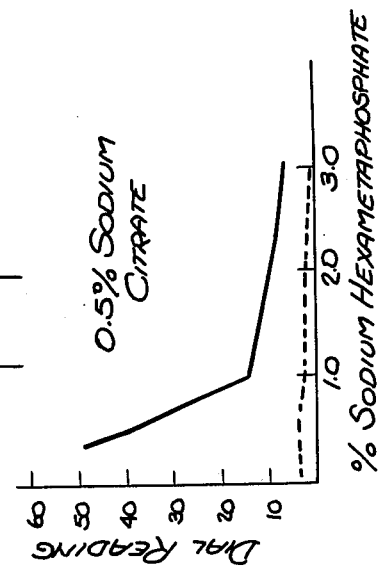
Fig. IIC.
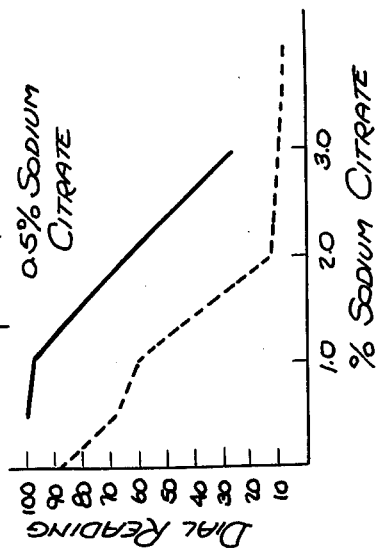
Fig. IIIC.
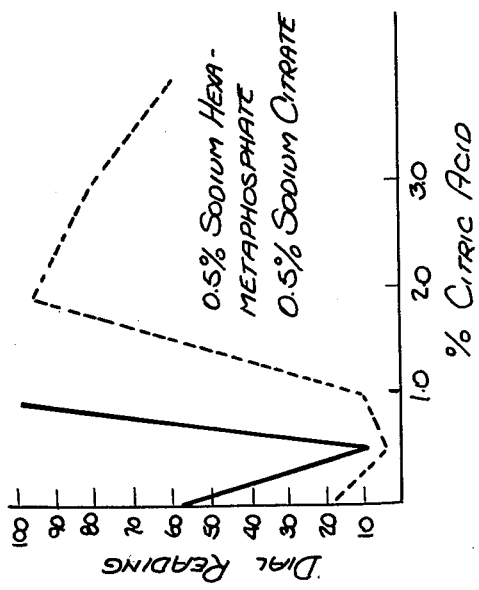
Fig. ID.
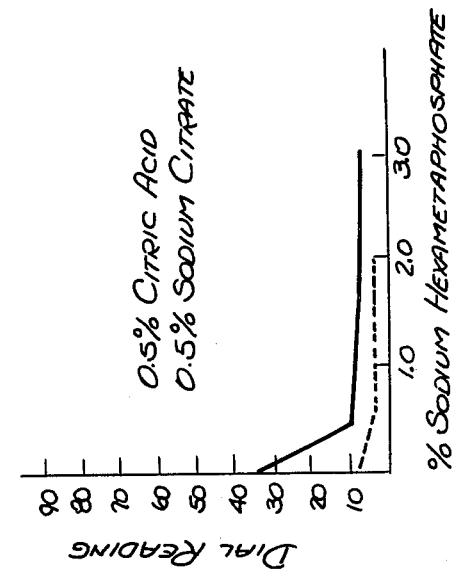
Fig. IID.
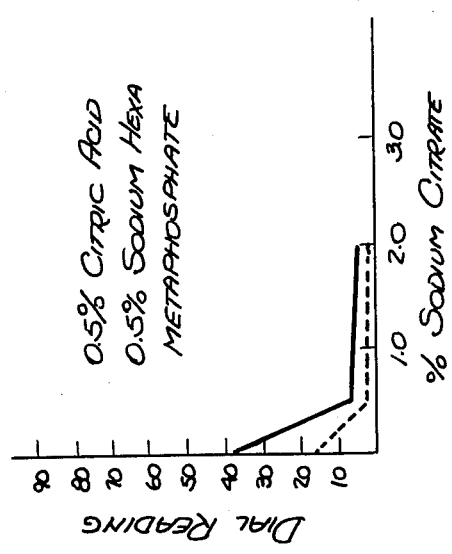
Fig. IIID.

CONCENTRATED MAGNESIUM HYDROXIDE PREPARATIONS

This application is a continuation-in-part of application Ser. No. 259,712, filed May 1, 1981, now abandoned, which is a continuation-in-part of application Ser. No. 872,995, filed Jan. 27, 1978, now abandoned, which is a continuation-in-part of application Ser. No. 724,454, filed Sept. 17, 1976, now abandoned.

The application relates to concentrated magnesium hydroxide preparations made from magnesium hydroxide pastes and to processes for making said preparations.

BACKGROUND OF INVENTION

Magnesium hydroxide suspensions with a relatively low concentration of magnesium hydroxide have been traditionally used as a laxative and an antacid and are commonly known as "milk of magnesia." The current USP edition defines "milk of magnesia" as a suspension of magnesium hydroxide, each 100 g of which contains not less than 7.0 g and not more than 8.5 g of $Mg(OH)_2$. It may contain 0.1 percent of citric acid, and may contain not more than 0.05 percent of a volatile oil or a blend of volatile oils, suitable for flavoring purposes.

The "milk of magnesia" preparations now on the market and made by diluting a magnesium hydroxide paste with water suffer from several major drawbacks in spite of being described as "stable suspensions." These preparations invariably separate into two (2) distinct layers with the clear aqueous layer forming the upper layer. The lower opaque layer is not uniform and contains increasing densities of the magnesium hydroxide as one goes from the top to the bottom. If the consumer fails to shake the bottle vigorously prior to use, he fails to obtain the desired dosage. If the marketed preparation of such a product is not used up in a relatively short time, then the partially used preparation presents even greater problems as the magnesium hydroxide paste tends to dry between the cap and the neck of the bottle and there ensues a slow and steady evaporation of water from the preparation, which sometimes results in a solid mass instead of the liquid suspension in the bottle. These separated preparations are difficult to reconstitute to a uniform constitution by gentle shaking, and frequently even prolonged vigorous shaking of such preparations will not result in a uniformly reconstituted product. The consumer tends to get a lower than intended dose upon initial use of the preparation and a higher than intended dose as the product is used up. Furthermore, the milk of magnesia products now on the market have poor "freeze-thaw" stability. These products also have an alkaline, chalky taste which prevents wide acceptance by the consumer.

The proposed FDA monograph on laxatives recommends a dosage of about 30 to 60 ml of milk of magnesia, i.e., the milk of magnesia preparations now on the market and containing from about 7.0 to 8.5 percent by weight of magnesium hydroxide. This amounts to taking about 6 to 12 teaspoons of the product at one time, which is inconvenient and unacceptable to some consumers. While more concentrated magnesium hydroxide preparations would solve this problem, such preparations having good stability and other desirable properties are not available.

It is accordingly a main object of the present invention to provide a process for the preparation of such pharmaceutically elegant concentrated magnesium hydroxide preparations.

It is another object of the present invention to provide a concentrated aqueous magnesium hydroxide preparation which does not readily settle or cake on standing.

It is still another object of the present invention to provide a concentrated aqueous magnesium hydroxide preparation which has freeze-thaw stability and is palatable.

It is a further object of the present invention to provide aqueous magnesium hydroxide preparations having the above-mentioned properties and containing from about 16 to 24 percent by weight/volume of magnesium hydroxide.

SUMMARY OF THE INVENTION

In accordance with the above objects of the present invention, we have discovered a stable aqueous thixotropic composition for the oral administration of magnesium hydroxide which composition has a viscosity immediately after manufacture of about 25 to 150 CPS as measured by a Brookfield-LVT viscometer with a No. 2 Spindle run at 30 RPM, and a yield value 24 hours after manufacture of about 5 to 14 as measured by a Haake Rotovisco RVIII viscometer at room temperature at 4 RPM with a 50 gram measuring head and comprises: magnesium hydroxide paste; a water-soluble pharmaceutically acceptable stabilizing or thixotropy producing agent selected from the group of polycarboxilic acids consisting of citric, tartaric, succinic, adipic, malic and fumaric acids; a water-soluble, pharmaceutically acceptable thinning or fluidizing agent selected from the group consisting of alkali and ammonium salts of phosphoric acids and salts of polycarboxilic acids selected from the group consisting citric, tartaric, succinic, adipic, malic, and fumaric acids, and mixtures of said salts; a water soluble, pharmaceutically acceptable anionic polymer selected from the group consisting of sodium carboxymethylcellulose, alginic acid derivatives such as sodium, potassium or propylene glycol alginates, and carrageenin; sucrose; and water.

The method of preparing the stable, thixotropic concentrated composition of the present invention requires a specific order of steps as follows:

1. an aqueous solution of the anionic polymer is prepared,
2. with mixing, a thinning or fluidizing agent is added thereto;
3. next, magnesium hydroxide paste is added and the mixture is stirred to a homogeneous suspension;
4. to the homogeneous suspension is added with mixing an aqueous solution of a stabilizing or thixotropy producing agent;
5. then, a thinning or fluidizing agent is added followed by addition of water with stirring to obtain a uniform suspension.

Optionally sucrose may be added in steps (1), (2) (3) or (4).

It has been suprisingly discovered that in preparing the composition of the present invention according to the prescribed order of steps, on addition to the composition being prepared the stabilizing or thixotropy producing agent, such as citric acid, increases the viscosity of the suspension to a gel-like consistency. This is contrary to the art-observed phenomenon where citric acid is used to thin or reduce viscosity of magnesium hydroxide suspensions to obtain a formulation having pourable consistency. Additions of about 0.08 to 1.0% by w/v of citric acid in the prescribed order and with the prescribed formula produces a thick gel which must be thinned with a thinning of fluidizing agent to obtain a thixotropic suspension. On gentle shaking the suspension becomes a fluid so that the same can be easily handled by the consumer. On standing the suspension again regains its gel-like consistency and remains homogeneous in the container without separation or settling of the suspended particles.

DETAILED DESCRIPTION OF THE INVENTION

The present invention provides a more concentrated form of the traditional milk of magnesia which overcomes all the disadvantages described above but retains the singular advantage of providing a markedly improved dosage form using magnesium hydroxide paste as the starting material. The improved product has a concentration of 16 to 24 percent weight/volume magnesium hydroxide and therefore, in the case of the 24 percent suspension, the volume of a dose can be reduced to one third. Thus, the product of the instant invention can be taken in amounts of only 2 to 4 teaspoonfuls to provide the same dose as now obtained from the lower concentrated preparations now on the market, a more acceptable volume to the consumer. The triple concentrated product can be put in much smaller bottles for the same number of doses and is thus significantly more portable and occupies less space in the bathroom cabinets, suitcases, etc. The concentrated product eliminates the need for packaging the milk of magnesia in familiar 32 oz. bottles.

Another desirable attribute of the preparation of the present invention is the fact that it shows little or no separation into opaque and clear layers. This provides the consumer not only with a more aesthetically appealing product, but more importantly a uniform dosage as the product, which is like a gel, becomes fluidlike water upon gentle shaking. This result was most unexpectedly achieved by following a prescribed order of addition of additives and will be fully described herein.

A further advantage of the new composition of this invention is the fact that the extreme stability of the product to a freeze-thaw cycle, which means that the suspension characteristics of the product are not destroyed upon freezing as invariably happens with the traditional milk of magnesia. Moreover, the product will not freeze even at $-15°$ C. and therefore can withstand shipping in unheated trucks to a much greater degree. Furthermore, since the product contains much less water, the expansion is relatively small even when the product is frozen, and the glass bottle containing the product will not crack if provided with ordinary head space as opposed to traditional milk of magnesia preparations which will make glass bottles crack upon freezing due to expansion.

Additionally, the product of the present invention has a much better and acceptable taste than the alkaline, chalky taste of the preparations now on the market.

The stable, thixotropic concentrated magnesium hydroxide formulation of the present invention is produced by a method having a specified order of addition of the essential components. Further, the formulation is substantially based on the suprising discovery that the stabilizing or thixotropy producing agents when used in preparing the product of the present invention, of which citric acid is preferred, behave in a manner contrary to that experienced by the prior art in making milk of magnesia preparations. This discovery is illustrated by Example 1, and FIGS. 1A through D, IIA through D and IIIA through D.

EXAMPLE 1

Citric Acid Concentration Series

| Base Formula | Percent |
|---|---|
| Ingredient | |
| 1022 HYDRO-MAGMA | 53.33/80.01 |
| Sodium Carboxymethyl Cellulose | 0.30 |
| Base Additive (A, B, C or D) | 0.50 |
| Water, qs. | 100.00 |
| Base Additives | |
| FIG. I-A, IIA & IIIA | 0.50 Sodium Hexametaphosphate |
| FIG. I-B, IIB & IIIB | 0.50 Citric Acid |
| FIG. I-C, IIC & IIIC | 0.50 Sodium Citrate |
| FIG. I-D, IID & IIID | 0.50 Sodium Hexametaphosphate and 0.50 Sodium Citrate |

Double strength formulations having increasing concentrations of citric acid shown in broken lines in FIGS. I-A through I-D, II-A through IID and III-A through IIID and triple strength formulations shown in solid lines in the same figures were prepared as follows: an amount of sodium carboxymethylcellulose as shown in Example 1, base formula, was added to a small amount of hot water and stirred with a Lightnin mixer set at top speed for 5 minutes. The mixer was stopped and the mixture let stand for 25 minutes while the sodium carboxymethylcellulose finished hydrating. After the polymer had hydrated, the mixture was stirred for 3 more minutes.

An amount of base additive as shown in Example 1 was dissolved in a minimum of hot water and added to the hydrated sodium carboxymethylcellulose. The mixture was stirred for 3 minutes.

Mixing was continued and an amount of HYDRO-MAGMA magnesium hydroxide (magnesium hydroxide sold under the trademark of HYDRO-MAGMA by Merck & Co., Inc.) paste as shown in Example 1 was added. This mixture was stirred for 3 minutes.

The mixer was stopped and the volume adjusted with additional water. Stirring was again begun and continued for 10 minutes. The viscosity of the base formula was then determined immediately after manufacture by a Brookfield LVT viscometer with appropriate spindle.

To generate FIGS. 1A through 1D increasing amounts of citric acid as a 50% solution was added. After each addition the mixture was stirred for 10 minutes and the viscosity taken and the dial reading was plotted v. % citric acid. From the results, the following conclusions can be drawn.

FIG. 1A

When the base formula (concentrated milk of magnesia with 16 or 24 percent magnesium hydroxide) contains small amounts of alkali salts of phosphoric acid (e.g. 0.50% sodium hexametaphosphate), the addition of increasing amounts of a polycarboxylic acid, such as citric acid, causes an initial drop in viscosity, followed by a dramatic rise in viscosity which is followed by a drop in viscosity (the last stage could not be measured under experimental conditions in the case of the base formula having 24 percent weight/volume magnesium hydroxide because it became impossible to mix).

FIG. 1B

When the base formula contains small amounts of a polycarboxylic acid (e.g. citric acid), the addition of increasing amounts of a polycarboxylic acid, such as citric acid, causes the formula to become increasingly thinner (viscosity decreases) up to a certain point and then additional amounts of citric acid have no further effect.

FIG. 1C

When the base formula contains an alkali polycarboxylate (e.g. 0.5% sodium citrate), addition of increasing amounts of polycarboxylic acid (e.g. citric acid) causes a drop in viscosity, followed by a rise in viscosity, which is then followed by a drop in viscosity. This effect is not as pronounced as in FIG. 1A. Additionally, this effect was only seen with a base formula containing 24% magnesium hydroxide but was not seen with the one containing 16% magnesium hydroxide.

FIG. 1D

In this case the base formula contains an alkali carboxylate as well as an alkali salt of a phosphoric acid. The effects are similar to that seen in FIG. 1A.

FIGS. IIA through IID

FIGS. IIA through IID contain increasing amounts of an alkali salt of phosphoric acid (e.g. sodium hexametaphosphate) under conditions similar to FIGS. 1A through 1D. The addition of increasing amounts of sodium hexametaphosphate results in an initial thinning effect to a certain point and then no further effect results.

FIGS. IIIA through IIID

FIGS. IIIA through IIID contain increasing amounts of sodium citrate under conditions similar to FIGS. IA through 1D and again the initial effect is a decrease in viscosity to a point and then further additions have no effect.

In view of the above, it is clear that the formulas shown in FIGS. I-A, I-C and I-D are prepared in accordance with the present invention and show the essential contribution of viscosity and thixotropy producing agents therein. All of the other formulas shown in this example were prepared for the purpose of comparison.

In accordance with the present invention, there are provided stable aqueous, thixotropic concentrated compositions containing in percent weight/volume:

| | |
|---|---|
| anionic polymer | 0.08 to 1.2 |
| thinning or fluidizing agent, e.g., sodium hexametaphosphate | 0.1 to 1.0 |
| magnesium hydroxide | 16 to 24 |
| stabilizing or thixotropy producing agent, e.g., citric acid | 0.05 to 0.8 |
| sucrose | 6 to 10 |
| thinning or fluidizing agent, e.g., sodium citrate | 0.05 to 0.8 |
| water | q.s. 100 vol. |

The preparations have a viscosity of about 25 to 150 CPS as measured by a Brookfield-LVT viscometer with a No. 2 spindle which is run at 30 RPM. The measurements are taken right after manufacture.

The preparations show substantially no separation and sedimentation after standing at room temperature for a period of at least a year. When some slight separation or sedimentation does occur, the preparations are readily reconstituted to uniformity by gentle shaking. The sedimentation studies were carried out as follows: the preparation, immediately after manufacture, is poured into a glass bottle with a screw top closure. The bottle is oblong in shape having a height of 9.8 cm and inside dimensions of 3.56 cm and 5.84 cm. The diameter of the neck is 2.79 cm. The bottled preparation was kept at room temperature and examined periodically.

The preparations were examined twenty-four hours after their preparation for their thixotropic properties with a Haake viscometer. The general principles and mode of operation are described in Remington's Pharmaceutical Sciences, 15th Ed., page 337. In taking these measurements, a flat paddle attachment was used with a Haake Rotovisco RVIII viscometer at room temperature, at 4 RPM with a 50 gram measuring head. The full scale on the chart was set to 25 scale units. The yield values were calculated as follows:

$$\frac{\text{Maximum peak height in cm.}}{\text{Distance from the zero point of each curve to full scale mark in cm.}} \times 25 \text{ scale units} =$$

Yield value in scale units.

The stable preparations of the present invention had yield values of 5 to 14 when thus measured and calculated.

If desired, sorbitol, glycerine, flavorants and preservatives can be added. These may be added to the composition in the following ranges:

| | |
|---|---|
| sorbitol (liquid USP) | 10 to 25 vol/vol |
| glycerine | 2 to 4 vol/vol |
| flavorants and preservatives | 0.3 to 0.7 wt/vol |

Sorbitol serves to increase shelf life and palatability, and glycerine serves to prevent cap locking. Suitable flavorants are peppermint oil, lemon oil and the like.

Suitable preservatives are methyl and propyl parabens.

While compositions outside the range of limitations stated herein possess many of the desirable characteristics of the present invention, such compositions will not, on extended shelf life, be sufficiently stable or lack optimum thixotropic quality. The significance of the two viscosity measurements and the values so obtained are explained briefly as follows:

"Thixotropy is the term used for liquids which flow freely if recently stirred, but gel on standing" (*Remington's Pharmaceutical Sciences*, 16th edition, pg 178, 1980).

Concentrated magnesium hydroxide is a system with large amounts of solid particles suspended in an aqueous medium. Such systems are common as pharmaceutical dosage forms.

An ideal pharmaceutical suspension has the following qualities:

1. Upon normal shaking it becomes fluid and easily pourable.
2. The suspended material does not settle at the bottom and cake as such sediments are very difficult to resuspend.
3. An aesthetically elegant suspension shows little or no separation of clear liquid at the top.

It is not uncommon to use two types of viscometers to characterize the viscosity of a complex system. It has been found that the Brookfield viscometer gives a reliable measure of the viscosity of a freshly prepared concentrated magnesium hydroxide while the Haake rotoviscometer characterizes it better upon standing. According to our experience if a concentrated magnesium hydroxide has a viscosity between 25 and 150 CPS immediately upon manufacture, when measured by the Brookfield LVT viscometer, and also a yield value between 5 and 14 measured by the Haake viscometer with a 24 hour old sample, and if the same preparations show little precipitation of solid particles in the specified bottle, then such preparations meet the criteria of an acceptable product with the desired thixotropic properties and shelf life.

The concentrated magnesium hydroxide when manufactured by the specified process and meeting the specified criteria, will ensure the desirable product. If the product has a viscosity of less than 25 CPS by the LVT Brookfield viscometer or it it also has a yield value of less than 5 by the Haake viscometer, then the viscosity of such a product is too low to hold up the particles in suspension and the undesirable sedimentation will occur at the bottom. On the other hand, if the viscosity of a freshly prepared concentrated milk of magnesia is greater than 150 CPS by the LVT Brookfield viscometer or also the yield value greater than 14 when measured by the Haake viscometer 24 hours after manufacture, then the viscosity of such a product is too high and hence its gel strength will be too high and it cannot be made fluid and pourable by simple shaking.

| | |
|---|---|
| magnesium hydroxide | 24 wt/vol |
| sorbitol liquid USP | 20 to 25 vol/vol |
| glycerine | 2.5 to 3.5 vol/vol |
| citric acid | 0.1 to 0.2 wt/vol |
| sodium citrate | 0.1 to 0.2 wt/vol |
| sodium hexametaphosphate | 0.25 to 0.35 wt/vol |
| anionic polymer | 0.20 to 0.40 wt/vol |
| sucrose | 7 to 8.5 wt/vol |
| flavorants and preservatives | 0.35 to 0.5 wt/vol |
| water | q.s. 100 vol |

The magnesium hydroxide is used in the form of an aqueous paste containing from about 29 to 32 percent by weight of magnesium hydroxide. The amount of paste calculated to provide the desired concentration of magnesium hydroxide is used. A preferred commercial preparation is HYDRO-MAGMA supplied by Merck & Company, Rahway, N.J. The specifications for this material are given in the Merck Product Data Bulletin for HYDRO-MAGMA.

The anionic polymer, sodium hexametaphosphate, and sodium citrate serve to provide the preparations with the desired viscosity and fluidity.

The anionic polymers should be pharmaceutically acceptable and water-soluble. In addition to exerting an effect on the viscosity, these polymers serve as suspending agents.

The anionic polymers that have been found particularly suitable are: sodium carboxymethylcellulose, sodium alginate, and sodium carrageenin. Other suitable anionic polymers are derivatives of guar gum, alginic acid, poly-acrylic acid, and the like.

The optimum amount of the anionic polymer will depend upon the choice of the polymer. The average chain length or degree of polymerization and the degree of substitution determine the viscosity produced. The polymer CMC-7MF ® is preferred. It is a sodium carboxymethylcellulose manufactured by Hercules, Inc. where "7" means the CMC used had 7 carboxymethyl groups for each 10 anhydroglucose units, "M" means it is a medium viscosity type with a degree of polymerization of 500 and a molecular weight of 100,000 and "F" means it is suitable for use in food, cosmetics, and pharmaceuticals. Thus when using CMC-7MF ®, it has been found that amounts of 0.1% to 1.0% weight/volume are preferable and the most preferred range falls between 0.25% and 0.35% weight/volume.

The sodium carboxymethylcellulose is preferably admixed with sugar prior to use.

The sodium hexametaphosphate serves as a thinning or fluidizing agent. While this compound is preferred, other salts such as alkali and ammonium salts of the different phosphoric acids, alkali and ammonium salts of polycarboxylic acids, and mixtures thereof may be used in place of the preferred sodium hexametaphosphate. Suitable salts of polycarboxylic acids include citric, tartaric, succinic, and adipic acids.

The citric acid serves to produce a stable thixotropic suspension. Other acids which may be used in place of citric acid include such pharmaceutically acceptable acids as tartaric, succinic, adipic, malic, fumaric and the like.

The sodium citrate acts as a thinning or fluidizing agent. While this is the preferred thinning agent, alkali metal or ammonium salts of other pharmaceutically acceptable polycarboxylic acids and phosphoric acids may be used in its place.

To obtain the compositions having the desired stability and thixotropic characteristics a process involving a specific order of addition of the materials must be followed in their preparation. In accordance with the present invention this process comprises the steps:

(i) preparing an aqueous solution of the desired amounts of the anionic polymer and the thinning or fluidizing agent;

(ii) adding with stirring to said aqueous solution the desired amount of the magnesium hydroxide paste to produce a suspension;

(iii) adding with stirring to said suspension an aqueous solution of the desired amount of the stabilizing or thixotropy producing agent;

(iv) optionally adding with stirring the desired amount of sugar or at any one of steps (i), (ii), or (iii);

(v) adding an additional amount of the thinning or fluidizing agent; and (vi) adding, with stirring, water to the desired volume and continuing the stirring until a uniform suspension is obtained.

When sorbitol or glycerine or flavorants or preservative are added, they may be added at any one of steps (i) to (iv).

The invention will be made clearer in the examples which follow. These examples are given by way of illustration and are not to be taken as limiting.

EXAMPLE 2

| Ingredient | Percent | Amount |
|---|---|---|
| Magnesium Hydroxide | 24.00 w/v | 1600.2 gm |
| Sorbitol Liquid USP | 22.00 w/v | 440.0 ml |
| Glycerine | 2.50 v/v | 50.0 ml |
| CMC-7MF | 0.30 w/v | 6.0 gm |
| Citric Acid, Anhydrous | 0.30 w/v | 6.0 gm |
| Sodium Citrate | 0.15 w/v | 3.0 gm |

-continued

| Ingredient | Percent | Amount |
| --- | --- | --- |
| Sodium Hexametaphosphate | 0.15 w/v | 3.0 gm |
| Granulated Sugar | 8.00 w/v | 160.0 gm |
| Flavorant and Preservatives | 0.40 w/v | 8.0 ml |
| Water Q.S. | 100.00 v | 2000.0 ml |

Viscosity, sedimentation and thixotropy measurements were carried out on the preparation of Example 2 as described above. The viscosity was 83 CPS. There was very little visible sedimentation or settling after the preparation stood for 4 months at room temperature. The yield value was 7.04.

EXAMPLE 3

Manufacturing Procedure for 24% Magnesium Hydroxide Suspension:

1. To a 2000 ml beaker add 440 ml of sorbitol liquid USP, 50 ml of glycerin, and 30 ml of sterile water. Heat to 90° C.
2. Premix 6.0 g CMC with 30 g of sugar and sprinkle into hot solution under Lightnin mixer. Mix for 5 minutes. Stop mixer and hydrate for an additional 25 minutes totaling 30 minutes. Note: If solution contains lumps of CMC, continue mixing until no lumps remain.
3. After 30 minutes of hydrating, add 10 g of sodium hexametaphosphate predissolved in 20 ml of hot water and mix for 3 minutes at 1000 RPM with Lightnin mixer.
4. Add the 1600.2 g hydromagma and mix using a speed of 1300 RPM for 3 minutes.
5. Transfer under the laboratory Gifford-Wood homomixer and mix for a total of 10 minutes using the full rheostat speed. Adjust plate so that the liquid mixes well without splashing.
   a. Add 6.0 g citric acid predissolved in 15 ml of hot water after 3 minutes of homomixing.
   b. Add 3.0 g sodium citrate predissolved in 15 ml of hot water after 6 minutes of homomixing.
   c. Slowly add the remaining 130.0 g sugar to the formula after 8 minutes of homomixing.
6. Remove and let cool to room temperature in a cold water bath.
7. When cooled, then place under Lightnin mixer and mix for 5 minutes at a speed of 1000 RPM.
8. Add flavor and preservative and mix for 1 minute.
9. Note volume and q.s. to 1000. Mix for 3 minutes.

The following six formulations were tested for sedimentation, viscosity and yield values in order to demonstrate with evidence the essential requirement of the order of addition in preparing the product of the invention. The six formulations contain all the ingredients in the amounts as in Example 2. The difference between the formulations lie in the order of addition of three of the essential ingredients, namely, sodium hexametaphosphate (a thinning or fluidizing agent), citric acid (a stabilizing or thixotropy producing agent), and sodium citrate (a thinning or fluidizing agent).

EXAMPLE 4

The formula of this example is the same as that of Example 2 and was prepared by the process of the present invention having the order of addition of three of the essential ingredients as follows:
(A) sodium hexametaphosphate
(B) citric acid
(C) sodium citrate In Examples 5, 6, 7, 8 and 9 the formula is the same as that of Example 2, however, the order of addition of three of the essential ingredients, namely (A) sodium hexametaphosphate, (B) citric acid and (C) sodium citrate were varied as indicated to cover all the possible permutations.

| EXAMPLE 5 | EXAMPLE 6 | EXAMPLE 7 | EXAMPLE 8 | EXAMPLE 9 |
| --- | --- | --- | --- | --- |
| BCA | CAB | CBA | BAC | ACB |

The result is shown in Table 1.

TABLE 1

Evaluation of Formulas of Examples 4–9

| Example | Order of Addition | Sedimentation | Viscosity Dial Reading Brookfield Spindle 2/30 RPM in CPS | Haake Rotoviscometer Yield Value |
| --- | --- | --- | --- | --- |
| 4 | A B C | very little | 83 | 7.04 |
| 5 | B C A | heavy | 40 | 0.56 |
| 6 | C A B | heavy | 57 | 0.78 |
| 7 | C B A | heavy | 29 | 0.74 |
| 8 | B A C | moderate | 59 | 2.39 |
| 9 | A C B | none | 164 | 8.56 |

The data shows that only the formula of Example 4, having the order of addition in accordance with the process of the present invention meets all three requirements, namely: no sedimentation or very little sedimentation; a viscosity in the range of 25–150 CPS measured by the Brookfield LVT Viscometer with Spindle No. 2/30 RPM; and a yield value in the range of 5–14 as measured by the Haake viscometer 24 hours after manufacture.

In view of the above, it will be seen that the objects of the invention are achieved. As various changes could be made without departing from the scope of the invention, it is intended that the above description be interpreted as illustrative and not in a limiting sense.

What is claimed is:

1. A stable aqueous thixotropic composition for the oral administration of magnesium hydroxide, said composition having a viscosity immediately after manufacture of about 25 to 150 CPS as measured by a Brookfield-LVT viscometer with a No. 2 Spindle run at 30 RPM, and a yield value 24 hours after manufacture of about 5 to 14 as measured by a Haake Rotovisco R VIII viscometer at room temperature at 4 RPM with a 50 gram measuring head comprising:

| | | |
| --- | --- | --- |
| (a) | magnesium hydroxide | 16–24% w/v |
| (b) | a water-soluble, pharmaceutically acceptable stabilizing or thixotropy producing agent selected from the group of polycarboxylic acids consisting of citric, tartaric, succinic, adipic, malic and fumaric acids | 0.05 to 0.8% w/v |
| (c) | a water-soluble, pharmaceutically acceptable thinning or fluidizing agent selected from the group consisting of alkali and ammonium salts of phosphoric acids and pharmaceutically acceptable salts of polycarboxylic acids selected from the group consisting of citric, tartaric, succinic, adipic, malic, and fumaric acids, and mixtures of said salts | 0.05 to 1.8 w/v |
| (d) | a water-soluble, pharmaceutically | 0.08 to 1.2 w/v |

-continued

| | | |
|---|---|---|
| | acceptable anionic polymer selected from the group consisting of sodium carboxymethylcellulose, alginic acid derivatives and carrageenin | |
| (e) | sucrose | 6 to 10 w/v |
| (f) | water | q.s 100 v. |

2. The composition of claim 1 wherein the thinning or fluidizing agent is sodium citrate.

3. The composition of claim 1 wherein said thinning or fluidizing agent is sodium hexametaphosphate.

4. The composition of claim 3 further comprising 20 to 25 v/v sorbitol liquid U.S.P.

5. The composition of claim 4 further comprising 2.5 to 3.5 v/v glycerin.

6. The composition of claim 5 further comprising 0.35 to 0.50 w/v flavorants and preservatives.

7. A stable aqueous thixotropic composition for the oral administration of magnesium hydroxide, said composition having a viscosity immediately after manufacture of about 25 to 150 CPS as measured by a Brookfield-LVT viscometer with a No. 2 spindle run at 30 RPM, and a yield value 24 hours after manufacture of about 5 to 14 as measured by a Haake Rotovisco R VIII viscometer at room temperature at 4 RPM with a 50 gram measuring head comprising:

| (a) | magnesium hydroxide | 16 to 24 w/v |
|---|---|---|
| (b) | citric acid | 0.05 to 0.8 w/v |
| (c) | sodium citrate | 0.05 to 0.8 w/v |
| (d) | sodium hexametaphosphate | 0.1 to 1.0 w/v |
| (e) | sodium carboxymethylcellulose | 0.08 to 1.2 w/v |
| (f) | sucrose | 7 to 8.5 w/v |
| (g) | water | q.s. to 100 v |

8. A stable aqueous thixotropic composition for the oral administration of magnesium hydroxide, said composition having a viscosity immediately after manufacture of about 25 to 150 CPS as measured by a Brookfield-LVT viscometer with a No. 2 spindle run at 30 RPM and a yield value 24 hours after manufacture of about 5 to 14 as measured by a Haake Rotovisco R VIII viscometer at room temperature at 4 RPM with a 50 gm measuring head comprising:

| | |
|---|---|
| magnesium hydroxide | 24% w/v |
| sorbitol liquid USP | 22% v/v |
| glycerine | 2.5% v/v |
| sodium carboxymethylcellulose | 0.3% w/v |
| citric acid | 0.3% w/v |
| sodium citrate | 0.15% w/v |
| sodium hexametaphosphate | 0.15% w/v |
| sucrose | 8.0% w/v |
| flavorant and preservatives | 0.4% w/v |
| water | q.s. 100 v. |

9. A process for the preparation of a stable, thixotropic composition for the oral administration of magnesium hydroxide which comprises in the order specified the steps of:
(a) preparing an aqueous solution of 0.08 to 1.2% w/v of an anionic polymer selected from the group consisting of sodium carboxymethylcellulose, alginic acid derivatives and carrageenin and 0.05 to 0.8% w/v of a thinning or fluidizing agent selected from the group consisting of alkali and ammonium salts of phosphoric acids and pharmaceutically acceptable polycarboxylic acid salts selected from the group consisting of citric, tartaric, succinic, adipic, malic, and fumaric acids, and mixtures of said salts;
(b) adding with stirring to said aqueous solution a magnesium hydroxide paste to obtain 16 to 24% w/v of magnesium hydroxide to produce a suspension;
(c) adding with stirring to said suspension an aqueous solution of 0.05 to 0.8% w/v of a stabilizing or thixotropy producing agent selected from the group of polycarboxylic acids consisting of citric, tartaric, succinic, adipic, malic and fumaric acids;
(d) adding with stirring to said suspension 6 to 10% of a sucrose at any one of steps (a), (b) or (c);
(e) adding to said suspension 0.1 to 1.0% w/v of a thinning or fluidizing agent to prevent gelling;
(f) adding to said suspension with stirring water to bring volume to 100; and
(g) stirring to obtain uniform suspension.

10. A process according to claim 9 wherein the stabilizing or thixotropy producing agent is citric acid.

11. A process according to claim 9 wherein the thinning or fluidizing agent is sodium citrate.

12. A process according to claim 9 wherein the thinning or fluidizing agent is sodium hexametaphosphate.

13. A process according to claim 9 wherein the anionic polymer is sodium carboxymethylcellulose.

14. A process according to claim 9 wherein the sucrose is added in step (a).

15. A process according to claim 9 wherein 2 to 4% v/v of glycerin and 10 to 25% v/v sorbitol are added with the sucrose.

16. A process according to claim 9 wherein, desired amounts of preservative and flavorant are added prior to step (e).

17. The stable, thixotropic composition for the oral administration of magnesium hydroxide made according to the process of claim 9.

18. A process for the preparation of a stable, thixotropic composition for the oral administration of magnesium hydroxide, which comprises in the order specified the steps of:
(a) preparing an aqueous solution of 0.08 to 1.2% w/v of sodium carboxymethylcellulose and 0.05 to 0.8% w/v of sodium citrate;
(b) adding with stirring to said aqueous solution a magnesium hydroxide paste to obtain 16 to 24% w/v magnesium hydroxide to produce a suspension;
(c) adding with stirring to said suspension an aqueous solution of 0.05 to 0.8% w/v citric acid;
(d) adding with stirring to said suspension 6 to 10% w/v of a sucrose at any steps (a.), (b.) or (c.);
(e) adding to said suspension 0.1 to 1.0% w/v of sodium hexametaphosphate;
(f) adding to said suspension with stirring water to bring volume to 100; and
(g) stirring to obtain uniform suspension.

19. The process of claim 18 wherein the sucrose is added at step (a).

20. The process of claim 18 wherein 2 to 4% w/v of glycerin and 10 to 25% v/v sorbitol are added with the sucrose.

21. The process of claim 18 wherein desired amounts of preservatives and flavorant are added prior to step (e).

22. The stable, thixotropic composition for the oral administration of magnesium hydroxide made according to the process of claim 18.

* * * * *